United States Patent [19]

Gubin et al.

[11] Patent Number: 5,508,431

[45] Date of Patent: Apr. 16, 1996

[54] 4-HYDROXYPHENYLTHIO DERIVATIVES, THEIR PREPARATION AND THEIR USE FOR THE PREPARATION OF AMINOALKOXYPHENYLSULPHONYL DERIVATIVES

[75] Inventors: Jean Gubin, Brussels; Henri Inion, Wemmel, both of Belgium

[73] Assignee: Elf Sanofi, Paris, France

[21] Appl. No.: 302,427

[22] Filed: Sep. 8, 1994

Related U.S. Application Data

[62] Division of Ser. No. 80,171, Jun. 23, 1993, Pat. No. 5,401,855.

[30] Foreign Application Priority Data

Jun. 23, 1992 [FR] France .................. 92 07659

[51] Int. Cl.⁶ .................. C07D 209/04
[52] U.S. Cl. .................. 548/484; 548/486; 549/52; 549/53; 549/55; 549/56; 549/466
[58] Field of Search .................. 548/484, 486; 549/52, 53, 55, 56, 466

[56] References Cited

U.S. PATENT DOCUMENTS

| | | | |
|---|---|---|---|
| 4,117,128 | 9/1978 | Brenner | 424/248.5 |
| 4,957,925 | 9/1990 | Gubin et al. | 514/299 |
| 5,017,579 | 5/1991 | Gubin et al. | 514/299 |
| 5,095,031 | 3/1992 | Brooks et al. | 548/484 |
| 5,124,327 | 6/1992 | Greenlee et al. | 548/484 |

FOREIGN PATENT DOCUMENTS

| | | |
|---|---|---|
| 0302792 | 2/1989 | European Pat. Off. . |
| 0382628 | 8/1990 | European Pat. Off. . |
| 0382629 | 8/1990 | European Pat. Off. . |
| 0302793 | 11/1990 | European Pat. Off. . |
| 0382618 | 11/1991 | European Pat. Off. . |

OTHER PUBLICATIONS

CA 111:97204r Preparation of . . . agents. Gubin et al. p. 741, 1989.

Chemical Abstract 107: 134155r (1987).

*Primary Examiner*—Joseph K. McKane
*Attorney, Agent, or Firm*—Jacobson, Price, Holman & Stern

[57] ABSTRACT

The subject of the invention is 4-hydroxyphenylthio derivatives of general formula:

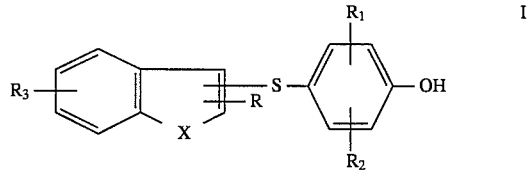

in which:

$R_1$ and $R_2$, which are identical or different, each represent hydrogen, a methyl or ethyl radical or a halogen atom, R represents a $(C_1-C_6)$ alkyl, $(C_3-C_6)$ cycloalkyl or phenyl radical, $R_3$ represents hydrogen or a halogen atom, X represents —O—, —S— or —$NR_4$— in which $R_4$ represents hydrogen or a $(C_1-C_4)$ alkyl group, useful as synthetic intermediates, especially for the preparation of aminoalkoxyphenylsulphonyl derivatives which are pharmaceutically active compounds.

1 Claim, No Drawings

4-HYDROXYPHENYLTHIO DERIVATIVES, THEIR PREPARATION AND THEIR USE FOR THE PREPARATION OF AMINOALKOXYPHENYLSULPHONYL DERIVATIVES

This application is a divisional of Ser. No. 08/080,171, filed Jun. 23, 1993, now U.S. Pat. No. 5,401,855.

The present invention relates generally to new substituted thiophenols, to a process for their preparation and to their use as synthetic intermediates.

More precisely, the subject of the invention is the 4-hydroxyphenylthio derivatives of general formula:

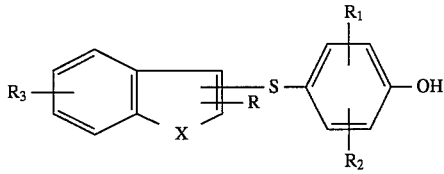

in which:
- $R_1$ and $R_2$, which are identical or different, each represent hydrogen, a methyl or ethyl radical or a halogen atom such as chlorine, bromine or iodine,
- R represents a $(C_1-C_6)$ alkyl, $(C_3-C_6)$ cycloalkyl or phenyl radical,
- $R_3$ represents hydrogen or a halogen atom such as chlorine or bromine,
- X represents —O—, —S— or —$NR_4$— in which $R_4$ represents hydrogen or a $(C_1-C_4)$ alkyl group.

Thus, taking account of the above values, R can especially represent a methyl, ethyl, n-propyl, isopropyl, n-butyl, n-pentyl, n-hexyl or cyclopropyl radical.

The compounds of formula 1 in which $R_1$ and $R_2$ each represent hydrogen, $R_3$ represents hydrogen or a chlorine atom and X represents a radical —$NR_4$— in which $R_4$ represents hydrogen or a methyl radical, constitute preferred compounds according to the invention.

Likewise, a particularly preferred series of compounds is represented by the formula I in which X represents a group —NR4—.

In the above formula I, the 4-hydroxyphenylthio group can be in position 2 of the heterocycle and the group R in position 3, or vice versa, so as to form substituted 3—R—2-(4-hydroxyphenylthio)benzofurans, -benzothiophenes or -indoles or substituted 2—R—3-(4-hydroxyphenylthio)benzofurans, -benzothiophenes or -indoles. However, the substituted 3—R—2-(4-hydroxyphenylthio)indoles of formula I are preferred.

The compounds of the invention are found to be particularly useful as intermediates, especially for the preparation of 4-hydroxyphenylsulphonyl derivatives of general formula:

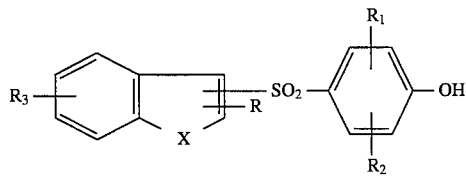

in which R, $R_1$, $R_2$, $R_3$ and X have the same meaning as above.

These compounds of formula II can be themselves widely used as intermediates in the preparation of various products, especially for the final synthesis of aminoalkoxyphenylsulphonyl derivatives of general formula:

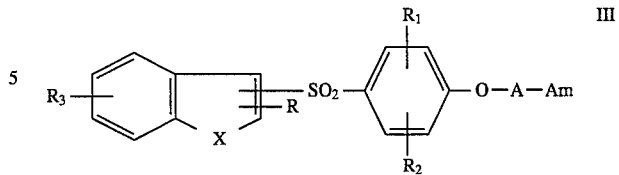

in which R, $R_1$, $R_2$, $R_3$ and X have the same meaning as above, A represents a $(C_2-C_5)$ alkylene or 2-hydroxypropylene radical, and Am represents a substituted amino radical, especially: -a radical of formula:

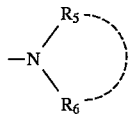

in which $R_5$ represents hydrogen or a $(C_1-C_8)$ alkyl radical and $R_6$ represents a $(C_1-C_8)$ alkyl radical or a radical of formula:

in which Alk represents a single bond or a $(C_1-C_5)$ alkylene radical and $R_7$ represents a pyridyl, phenyl, 2,3-methylenedioxyphenyl or 3,4-methylenedioxyphenyl radical or a phenyl group substituted by one or a number of identical or different substituents selected from halogen atoms, $(C_1-C_4)$ alkyl groups or $(C_1-C_4)$ alkoxy groups or $R_5$ and $R_6$, when they are taken together, represent a $(C_3-C_6)$ alkylene or alkenylene radical, optionally interrupted by —O—, —NH—, —N= or —$NR_8$—, $R_8$ representing a $(C_1-C_4)$ alkyl, phenyl or diphenylmethyl radical, so that $R_5$ and $R_6$, taken with the nitrogen atom to which they are attached, can especially represent a pyrrolidinyl, piperidinyl, morpholinyl, piperazinyl, 4-methylpiperazinyl, 4-phenylpiperazinyl or 1H-imidazolyl radical, -a group of formula:

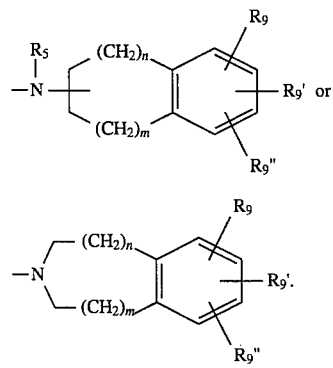

in which $R_5$ has the same meaning as above, $R_9$, $R'_9$ and $R''_9$, which are identical or different, each represent hydrogen, a halogen atom, such as chlorine or bromine, or a $(C_1-C_4)$ alkyl or $(C_1-C_4)$ alkoxy group, and n and m, which are identical or different, each represent 0, 1, 2 or 3, and for the preparation of their pharmaceutically acceptable salts.

Such aminoalkoxyphenylsulphonyl derivatives of formula III have been described, especially in Patents or Patent Applications EP-A-0,302,793, 0,382,618, 0,382,628 and 0,382,629.

These compounds have been shown to be particularly advantageous for their therapeutical applications, especially for their inhibiting properties on calcium translocation and for their bradycardic, hypotensive or antiadrenergic properties which make them useful in the treatment of certain pathological syndromes of the cardiovascular system, in particular in the treatment of angina pectoris, hypertension, arrhythmia or cerebral circulatory insufficiency. In the antitumour field, these compounds may be useful as anticancer potentiation agents.

There may be mentioned, as particularly representative compounds of this series of aminoalkoxyphenylsulphonyl derivatives:

1-methyl-3-isopropyl-2-[4-{3-[ N-methyl-N-(3,4-dimethoxy-β-phenethyl)amino] propoxy}phenylsulphonyl]] indole and its pharmaceutically acceptable salts (Compound A).

1-methyl-3-isopropyl-2-[4-{3-[ N-methyl-N-(3,5-dimethoxy-β-phenethyl)amino] propoxy}phenylsulphonyl]] indole and its pharmaceutically acceptable salts (Compound B).

2-[4-{3-[N-Methyl-N-(3,4-dimethoxy-β-phenethyl)amino]propoxy} phenylsulphonyl]-5-chloro-3-isopropyl-1-methylindole and its pharmaceutically acceptable salts (Compound C).

There has been reported, in the abovementioned patents, a process for the preparation of heterocyclic aminoalkoxyphenylsulphonyl derivatives starting from heterocyclic 4-hydroxyphenylsulphonyl derivatives, especially 4-hydroxyphenylsulphonyl derivatives of benzofuran, benzothiophene or indole. Additionally, there has been mentioned therein a method for the synthesis of these 4-hydroxyphenylsulphonyl derivatives. This especially includes an oxidation reaction of a heterocyclic 4-methoxyphenylthio derivative by means of 3-chloroperbenzoic acid.

Patent Application EP-A-0,302,793 describes, for example, the 4-stage synthesis of 3-isopropyl-1-methyl-2-(4-hydroxyphenylsulphonyl)indole starting from 3-isopropylindole according to a process involving an oxidation reaction of this type.

This process consists in:

a) coupling 3-isopropylindole with 4-methoxybenzenethiol to give 3-isopropyl-2-(4-methoxyphenylthio)indole (yield: 72% of pure product);

b) oxidising this compound with 3-chloroperbenzoic acid to give 3-isopropyl-2-(4-methoxyphenylsulphonyl)indole (yield: 90%);

c) methylating the compound obtained by means of methyl iodide in the presence of sodium hydride, which provides 1-methyl-3-isopropyl-2-(4-methoxyphenylsulphonyl)indole (yield: 85%);

d) O-deprotecting this compound by means of 2-mercaptoethanol/sodium hydride to finally produce the desired compound (yield: 45.9%).

Consequently, 3-isopropyl-1-methyl-2-(4-hydroxyphenylsulphonyl)indole can be synthesised according to this process with but a low overall yield of approximately 28% from 3-isopropylindole.

Additionally, the use of 2-mercaptoethanol leaves a nauseating smell in the 4-hydroxyphenylsulphonyl derivative of formula II, a smell which is found in the final aminoalkoxyphenylsulphonyl derivative of formula III.

The method thus described is especially characterised by the use of an oxidation stage of a phenylthio derivative containing a protected hydroxyl radical, in this case a methoxy radical, a protected hydroxyl radical which it is necessary to deprotect subsequently in the process so as to regenerate the free hydroxyl.

This use according to an oxidation/deprotection pair can be explained by the fact that the free hydroxyl functional group is well known to be sensitive to oxidising agents since it is capable of being oxidised fairly easily [Methoden der Organischen Chemie (Houben-Weyl), Band V1/1c - Phenole Teil 2, page 1121].

The search for an industrial process for the preparation of heterocyclic 4-hydroxyphenylsulphonyl derivatives of formula II using readily available and inexpensive synthetic intermediates with a satisfactory yield of final product remains of undeniable interest.

Now, it has been surprisingly discovered, according to the invention, that it is possible to produce heterocyclic 4-hydroxyphenylsulphonyl indole derivatives, especially 2- or 3-(4-hydroxyphenylsulphonyl) derivatives, with excellent yields by oxidation of heterocyclic phenylthio derivatives containing not a protected hydroxyl radical but a free hydroxyl radical.

According to the invention, the compounds of formula II are prepared by oxidising a phenylthio derivative of formula I by means of a suitable oxidising agent such as, for example, 3-chloroperbenzoic acid or magnesium monoperphthalate, and in an a suitable solvent, which provides the desired compounds.

Generally, the oxidation takes place at a temperature between −5° C. and room temperature, preferably at a temperature between 0° C. and room temperature.

As for the solvent, it can be a polar solvent containing an amido group, for example N,N-dimethylformamide, N,N-dimethylacetamide, 2-methylpyrrolidone or hexamethylphosphoric triamide, a lower alcohol, for example methanol or ethanol, or also a nitrile, such as acetonitrile.

N,N-Dimethylformamide constitutes a particularly preferred solvent.

Generally, 2 to 2.5 equivalents of oxidising agent, preferably 3-chloroperbenzoic acid or magnesium monoperphthalate, are used per equivalent of compound of formula I.

Additionally, it is possible to envisage buffering the reaction mixture by introducing a weak base such as an alkali metal or alkaline-earth metal carbonate or bicarbonate.

The compounds of formula I can very advantageously give access to the compounds of formula II while avoiding the disadvantages of the prior processes.

In effect, the formation of a 4-hydroxyphenylsulphonyl chain from 4-hydroxyphenylthio derivatives of formula I can be carried out by means of a single reaction, in contrast to the prior processes which require the use of a two-fold reaction, that is to say first an oxidation and then a deprotection of the hydroxyl radical.

Additionally, the compounds of formula I make possible the synthesis of compounds of formula II with particularly advantageous yields considerably greater than those obtained according to the prior technique.

For example, 1-methyl-3-isopropyl-2-(4-hydroxyphenylsulphonyl)indole can be prepared from 3-isopropylindole via 2-(4-hydroxyphenylthio)-1-methyl-3-isopropylindole by using three stages, in contrast to the prior technique which requires four stages in all. Moreover, the overall yields obtained according to the invention prove to be greater than those provided by the known processes since they are of the order of 65% to 70% from 3-isopropylindole.

Consequently, 4-hydroxyphenylthio derivatives of formula I are also within the invention, as novel industrial products, useful especially as synthetic intermediates, for example for the preparation of 4-hydroxyphenylsulphonyl derivatives of formula II.

The compounds of formula I can be obtained by reacting a compound of general formula:

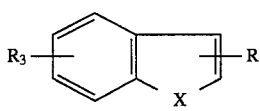
IV in which R, R₃ and X have the same meaning as above, with a thiophenol of general formula:

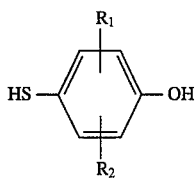
V in which $R_1$ and $R_2$ have the same meaning as above, in a suitable solvent such as an aqueous solvent containing a ($C_1$–$C_4$) alcohol, for example ethanol, or an amide such as N,N-dimethylformamide or hexamethylphosphoric triamide, in the presence of iodine and preferably at the reflux temperature of the reaction mixture, to produce the desired compounds.

The compounds of formula IV and V are known compounds which can be obtained according to known methods.

For example, the compounds of formula IV in which X represents a radical —NR₄—, in which R₄ is other than hydrogen, can be obtained by treating a compound of formula IV in which X represents —NH—, optionally in the form of a metal derivative, with a halide of general formula:

Hal—R₄     VI in which Hal represents a halogen atom, for example iodine, and R₄ has the same meaning as above except for hydrogen.

Preferentially, a metal derivative of the compound of formula IV in which X represents —NH— is used, which metal derivative is obtained by treating the compound of formula IV in question in which X represents —NH— with an alkali metal hydride or alkoxide, such as sodium hydride or potassium tert-butoxide.

As shown above, the 4-hydroxyphenylthio derivatives of formula I can be used for the preparation of aminoalkoxyphenylsulphonyl derivatives of formula III.

Consequently, 4-hydroxyphenylthio derivatives of formula I are also within the invention as intermediates for the final synthesis of aminoalkoxyphenylsulphonyl derivatives of formula III, in particular for the synthesis of Compounds A, B or C.

For example, it is possible to prepare the compounds of formula III starting from a 4-hydroxyphenylsulphonyl derivative of formula II itself obtained according to the invention from the 4-hydroxyphenylthio derivative of formula I, by use of a process containing the following sequence of stages:

a) coupling the compound of formula II, in the presence of a basic agent, with a dihaloalkane of general formula:

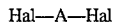
Hal—A—Hal     VII in which A has the same meaning as above and Hal represents a halogen atom, preferably bromine, at reflux in a suitable solvent, generally a polar or nonpolar solvent such as methyl ethyl ketone, N,N-dimethylformamide, benzene, toluene or a xylene, or else b₁) coupling a halogenated alcohol of general formula:

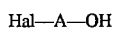
Hal—A—OH     VIII in which A and Hal have the same meaning as above, in a solvent such as N,N-dimethylformamide and in the presence of a basic agent, and then coupling the substituted alcohol obtained with a halide of general formula:

Hal—W     IX in which Hal has the same meaning as above and W represents a ($C_1$–$C_4$) alkylsulphonyl, for example methanesulphonyl, or ($C_6$–$C_{10}$) arylsulphonyl, for example phenylsulphonyl or p-toluenesulphonyl, radical, in an acid-accepting solvent, for example pyridine, or else b₂) heating at reflux with an epihalohydrin, such as epichlorohydrin, in the presence of a basic agent and in a polar solvent such as methyl ethyl ketone, to produce the heterocyclic sulphonyl derivatives of general formula:

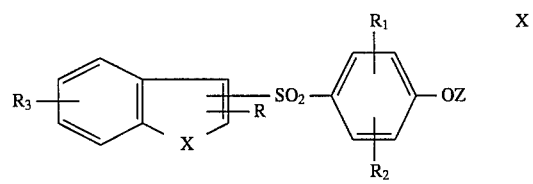
X in which R, $R_1$, $R_2$, $R_3$ and X have the same meaning as above and Z represents a radical of general formula:

—A—Z₁ in which A has the same meaning as above and Z₁ represents a halogen atom or a ($C_1$–$C_4$) alkylsulphonyloxy or ($C_6$–$C_{10}$) arylsulphonyloxy radical.

The basic agent used during the treatment of the compound of formula II is generally an alkali metal carbonate, for example potassium carbonate, an alkali metal hydroxide such as sodium hydroxide or potassium hydroxide, an alkali metal hydride such as sodium hydride, or an alkali metal alkoxide, for example sodium methoxide or sodium ethoxide.

The derivative of formula X is then reacted with an amine of general formula:

H—Am     XI in which Am has the same meaning as above, the reaction taking place in the presence of an acid acceptor and in a suitable solvent, generally a polar solvent such as an alcohol, for example butanol, a ketone such as methyl ethyl ketone, an aromatic hydrocarbon, for example benzene, toluene or a xylene, or even an excess of amine of formula XI, to produce the compounds of formula III in the form of a free base, which can be reacted, if desired, with a suitable acid to form a pharmaceutically acceptable salt of this compound.

According to an alternative method, it is possible to use the compounds of formula II obtained according to the invention by directly treating such a compound with a halide of general formula:

Hal—A—Am     XII in which Hal and Am have the same meaning as above and A represents a ($C_2$–$C_5$) alkylene radical, the reaction being carried out in the presence of a basic agent such as an alkali metal carbonate, for example potassium carbonate, an alkali metal hydroxide such as sodium hydroxide or potassium hydroxide, an alkali metal hydride such as sodium hydride, or an alkali metal alkoxide, for example sodium methoxide or sodium ethoxide, to produce the compounds of formula III in which A represents a ($C_2$–$C_5$) alkylene radical, which compound can be reacted, if desired, with a suitable acid to form a pharmaceutically acceptable salt of this compound.

The following, non-limiting examples illustrate the preparation of the compounds of the invention:

EXAMPLE 1

Preparation of 2-(4-hydroxyphenylthio)-3-isopropyl 1-methylindole a) 3-Isopropyl-1-methylindole A solution of 25 g (0.157 mol) of 3-isopropylindole in 200 ml of benzene is added to a suspension of 21.1 g (0.172 mol) of potassium tert-butoxide with good stirring.

24.51 g (0.172 mol) of methyl iodide are then slowly added. Stirring is continued at room temperature for 20 h.

A water/crushed ice mixture is added and the benzene fraction is separated. This fraction is washed twice with water, dried over anhydrous sodium sulphate, filtered and the solvent driven off on a rotary evaporator, which provides an oily residue.

In this way, 27 g of 3-isopropyl-1-methylindole are obtained.

Yield: 100%.

b) 2-(4-Hydroxyphenylthio)-3-isopropyl-1-methylindole 27 g (0.155 mol) of 3-isopropyl-1-methylindole and 21.7 g (0.172 mol) of 4-hydroxybenzenethiol are dissolved in 250 ml of ethanol and 125 ml of water. The whole is placed under a nitrogen atmosphere and a solution of 43.65 g (0.172 mol) of iodine in ethanol is slowly added. The mixture is heated at reflux for 2 hours, cooled and poured into ice-cold water. Extraction is carried out with ethyl acetate and the extract is washed with water and dried over anhydrous sodium sulphate. Filtration is then carried out, the solvent is evaporated on a rotary evaporator and purification is carried out by column chromatography (eluent: 7/3 heptane/dichloroethane).

In this way, there is obtained 33.9 g of 2-(4-hydroxyphenylthio)-3-isopropyl-1-methylindole.

Yield: 73.5%
M.p.: 89°–90° C.
Purity: 99.3%.

EXAMPLE 2

Preparation of 3-(4-hydroxyphenylthio)-2-isopropylindole 3.2 g (0.02 mol) of 2-isopropylindole and 2.5 g (0.02 mol) of 4-hydroxybenzenethiol are dissolved in 80 ml of ethanol.

40 ml of water are added, the mixture is stirred and then a solution of 5 g (0.04 mol) of iodine in ethanol is introduced dropwise. The oil thus formed is then poured into 400 ml of water and the mixture is then stirred while cooling until the oil has solidified. The product is filtered and washed on a filter. The product is then dried under vacuum at a temperature of 60° C., which provides 5.6 g of the expected product. Recrystallisation is then carried out from 250 ml of a 7/3 heptane/toluene mixture.

In this way, there is obtained 4.2 g of 3-(4-hydroxyphenylthio)-2-isopropylindole in the form of an insoluble resin.

Yield: 74.2%
M.p.: 116° C.

The following non-limiting examples illustrate the use of the compounds of the invention:

EXAMPLE I

Preparation of 2-(4-hydroxyphenylsulphonyl)-3-isopropyl 1-methylindole 13.17 g (0.044 mol) of 2-(4-hydroxyphenylthio)- 3-isopropyl-1-methylindole are dissolved in 70 ml of N,N-dimethylformamide. The solution is stirred and cooled to 0° C. and then a solution of 21.7 g (0.088 mol) of 70% 3-chloroperbenzoic acid is slowly (2 h) added. The temperature of the mixture is left to return to room temperature and stirring of the reaction mixture is continued for 20 h while monitoring the development of the reaction (sulphide, sulphoxide, sulphone) by T.L.C. The mixture is run into ice-cooled water and the precipitate formed is filtered and washed on the filter with a sodium bicarbonate solution, ending with water. Purification is then carried out by chromatography on a silica column (eluent: dichloroethane containing 2% of methanol).

In this way, there is obtained 9 g of 2-(4-hydroxyphenylsulphonyl)-3-isopropyl-1-methylindole.

Yield: 62.1%.
M.p.: 188° C.

EXAMPLE II

Preparation of 2-(4-hydroxyphenylsulphonyl)-3-isopropyl- 1-methylindole

By using the same process as that described in Example I but by adding, over 2 h at room temperature, 2.1 mol of 3-chloroperbenzoic acid to 1 mol of 2-(4-hydroxyphenylthio)-3-isopropyl-1-methylindole in N,N-dimethylformamide and by keeping the reaction mixture stirring for 24 h at room temperature, there is obtained 2-(4-hydroxyphenylsulphonyl)-3-isopropyl-1-methylindole with a yield of 62%.

EXAMPLE III

Preparation of 2-(4-hydroxyphenylsulphonyl)-3-isopropyl- 1-methylindole

By using the same process as that described in Example I but by adding, over 5 h at 10° C., 2.4 mol of 3-chloroperbenzoic acid to 1 mol of 2-(4-hydroxyphenylthio)-3-isopropyl-1-methylindole in N,N-dimethylformamide and by keeping the reaction mixture stirring for 48 h at room temperature, there is obtained 2-(4-hydroxyphenylsulphonyl)-3-isopropyl-1-methylindole with a yield of 80%.

EXAMPLE IV

Preparation of 2-(4-hydroxyphenylsulphonyl)-3-isopropyl- 1-methylindole

By using the same process as that described in Example I but by adding 2.4 mol of 3-chloroperbenzoic acid to 1 mol of 2-(4-hydroxyphenylthio)-3-isopropyl- 1-methylindole in N,N-dimethylformamide, at the rate of 1.1 mol over 0.5 h at 10° C. and then 1.3 mol over 5 h at 10° C., and by keeping the reaction mixture stirring for 48 h at room temperature, there is obtained 2-(4-hydroxyphenylsulphonyl)-3-isopropyl-1-methylindole with a yield of 88%.

EXAMPLE V

Preparation of the acid oxalate of 1-methyl-3-isopropyl-2-[4-{3-[N-methyl-N-(3,4-dimethoxy-β-phenethyl)amino]propoxy}phenylsulphonyl]indole 29 g (0.21 mol) of anhydrous and finely ground potassium carbonate are added to a mixture of 9.9 g (0.003 mol) of 2-(4-hydroxyphenylsulphonyl)-3-isopropyl-1-methylindole in 165 ml of N,N-dimethylformamide. The mixture is stirred for 0.5 hour and 13.3 g (0.033 mol) of the acid oxalate of 90% 1-chloro-3-[ N-methyl-N-(3,4-dimethoxy-β-phenethyl)amino]propane are added.

The mixture is heated at 100° C. for 1 hour and is left to return to room temperature with stirring. It is poured into 450 ml of water and ice and the mixture is stirred for 0.25 hour. Extraction is carried out with 3 times 150 ml of diethyl ether, and the extracts are washed twice with 150 ml of water and dried over sodium sulphate. 3.5 g of oxalic acid, dissolved in 50 ml of ethyl ether, are added to the ether solution obtained and the mixture is left to crystallise for 24 hours. The crystals are filtered, washed with isopropyl ether and dried under vacuum at 50° C.

In this way, there is obtained the acid oxalate of 1-methyl-3-isopropyl-2-[4-{3-[ N-methyl-N-(3,4-dimethoxy-β-phenethyl)amino]propoxy}phenylsulphonyl]indole.

Yield: 90%

M.p.: 94° C.

EXAMPLE VI

Preparation of 3-(4-hydroxyphenylsulphonyl)-2-isopropylindole 0.36 g (0.00127 mol) of 3-(4-hydroxyphenylthio)-2-isopropylindole are dissolved in 5 ml of N,N-dimethylformamide. The solution is cooled to 0° C. (ice bath) and a solution of 0.62 g (0.00254 mol) of 70% 3-chloroperbenzoic acid in 2 ml of N,N-dimethylformamide is added dropwise.

Stirring is continued at room temperature for 24 hours and then the mixture is run into ice-cold water.

The sticky precipitate thus formed is extracted with theyl acetate and the solution is washed with an aqueous sodium bicarbonate solution and then with water. The solution is dried over sodium sulphate, filtered and the solvent is driven off on a rotary evaporator, which provides a 0.5 g residue which is crystallised from an ethanol/water mixture.

In this way, there is obtained 0.38 g of 3-(4-hydroxyphenylsulphonyl)-2-isopropylindole.

Yield: 95%.

M.p.: 152° C.

We claim:

1. Process for the preparation of an aminoalkoxyphenyl compound of the general formula:

$$R_3 \text{-indole-}R\text{-}SO_2\text{-phenyl}(R_1)(R_2)\text{-}O\text{-}A\text{-}Am \quad \text{III}$$

in which R is selected from the group consisting of $(C_1\text{-}C_6)$alkyl, $(C_3\text{-}C_6)$cycloalkyl and phenyl, $R_1$ and $R_2$, which are identical or different, are selected from the group consisting of hydrogen, methyl, ethyl and halogen, X is selected from the group consisting of —O—, —S— and —NR$_4$— in which R$_4$ is selected from the group consisting of hydrogen and $(C_1\text{-}C_4)$alkyl, A is selected from the group consisting of $(C_2\text{-}C_5)$ alkylene and 2-hydroxypropylene, and Am represents substituted amino, comprising the steps of:

i) obtaining a 4-hydroxyphenylsulphonyl compound of the general formula:

$$R_3\text{-indole-}R\text{-}SO_2\text{-phenyl}(R_1)(R_2)\text{-}OH \quad \text{II}$$

in which R, $R_1$, $R_2$, and X have the same meaning as above, and $R_3$ is selected from the group consisting of hydrogen and halogen, by oxidizing a 4-hydroxyphenylthio compound of the general formula:

$$R_3\text{-indole-}R\text{-}S\text{-phenyl}(R_1)(R_2)\text{-}OH \quad \text{I}$$

in which R, $R_1$, $R_2$, $R_3$ and X have the same meaning as above, the oxidation taking place in a solvent by means of an oxidizing agent;

ii) coupling, in the presence of a basic agent, the 4-hydroxyphenylsulfonyl compound with either:

a) a dihaloalkane of general formula:

$$\text{Hal—A—Hal} \quad \text{VII}$$

in which A has the same meaning as above and Hal represents halogen, to produce a heterocyclic sulphonyl compound of the general formula:

$$R_3\text{-indole-}R\text{-}SO_2\text{-phenyl}(R_1)(R_2)\text{-}OZ \quad \text{X}$$

in which R, $R_1$, $R_2$, $R_3$ and X have the same meaning as above and Z represents a radical of general formula:

$$A—Z_1$$

in which A has the same meaning as above and $Z_1$ represents halogen, which phenylsulphonyl compound of formula X is reacted with an amine of general formula:

$$\text{H—Am} \quad \text{XI}$$

in which Am has the same meaning as above, the reaction taking place in the presence of an excess of amine of formula XI, to produce the aminoalkoxyphenyl compound in the form of a free base; or b) a halogenated alcohol of general formula $$\text{Hal—A—OH} \quad \text{VIII}$$

in which A and Hal have the same meaning as above, in a solvent, and the substituted alcohol obtained is then coupled with a halide of general formula:

$$\text{Hal—W} \qquad \qquad \text{IX}$$

in which Hal has the same meaning as above and W is selected from the group consisting of $(C_1-C_4)$ alkylsulphonyl and $(C_6-C_{10})$ arylsulphonyl, in an acid-accepting solvent to produce a heterocyclic sulphonyl compound of the general formula X in which $Z_1$ is selected from the group consisting of $(C_1-C_4)$ alkylsulphonyloxy and $(C_6-C_{10})$ arylsulphonyloxy, which phenylsulphonyl compound of formula X is reacted with an amine of general formula XI, the reaction taking place in the presence of an excess of amine of formula XI, to produce the aminoalkoxyphenyl compound in the form of a free base; or c) an epihalohydrin in a polar solvent and under reflux, to produce a heterocyclic sulphonyl compound of the general formula X in which $Z_1$ represents halogen, which phenylsulphonyl compound of formula X is reacted with an amine of formula XI, to produce the aminoalkoxyphenyl compound in the form of a free base; or d) with a halide of general formula:

$$\text{Hal—A—Am} \qquad \qquad \text{XII}$$

in which A, Hal and Am have the same meaning as above, to produce the aminoalkoxyphenyl compound in the form of a free base;

the free base so obtained being, if desired, reacted with an acid to form a pharmaceutically acceptable salt of the compound.

* * * * *